United States Patent
Kraus et al.

[11] Patent Number: 5,928,182
[45] Date of Patent: Jul. 27, 1999

[54] PEDIATRIC PROGRAMMABLE HYDROCEPHALUS VALVE

[75] Inventors: Robert G. Kraus, Attleboro; Bhupendra C. Patel, Mansfield; Robert W. Pike, Marshfield, all of Mass.

[73] Assignee: Johnson & Johnson Professional, Inc., Raynham, Mass.

[21] Appl. No.: 08/887,045

[22] Filed: Jul. 2, 1997

[51] Int. Cl.⁶ ................................................ A61M 5/00
[52] U.S. Cl. ........................................................ 604/9
[58] Field of Search ........................... 604/7–10, 4–6

[56] References Cited

U.S. PATENT DOCUMENTS

| | | | |
|---|---|---|---|
| 3,886,948 | 6/1975 | Hakim | 128/350 V |
| 4,206,761 | 6/1980 | Cosman | 128/660 |
| 4,206,762 | 6/1980 | Cosman | 128/660 |
| 4,281,666 | 8/1981 | Cosman | 128/748 |
| 4,281,667 | 8/1981 | Cosman | 128/748 |
| 4,332,255 | 6/1982 | Hakim et al. | 128/350 V |
| 4,382,445 | 5/1983 | Sommers | 604/8 |
| 4,387,715 | 6/1983 | Hakim et al. | 604/9 |
| 4,443,214 | 4/1984 | Marion | 604/9 |
| 4,551,128 | 11/1985 | Hakim et al. | 604/9 |
| 4,589,287 | 5/1986 | Dickens | 73/727 |
| 4,595,390 | 6/1986 | Hakim et al. | 604/9 |
| 4,615,691 | 10/1986 | Hakim et al. | 604/9 |
| 4,653,508 | 3/1987 | Cosman | 128/748 |
| 4,660,568 | 4/1987 | Cosman | 128/748 |
| 4,673,384 | 6/1987 | Marion | 604/10 |
| 4,676,772 | 6/1987 | Hooven | 604/9 |
| 4,741,730 | 5/1988 | Dormandy, Jr. et al. | 604/9 |
| 4,772,257 | 9/1988 | Hakim et al. | 604/9 |
| 4,781,673 | 11/1988 | Watanabe | 604/9 |
| 4,787,886 | 11/1988 | Cosman | 604/9 |
| 4,787,887 | 11/1988 | Arroyo | 604/9 |
| 5,000,731 | 3/1991 | Wong et al. | 604/8 |
| 5,054,518 | 10/1991 | Rancani | 137/516.27 |
| 5,069,663 | 12/1991 | Sussman | 604/9 |
| 5,154,693 | 10/1992 | East et al. | 604/9 |
| 5,167,615 | 12/1992 | East et al. | 604/9 |
| 5,176,627 | 1/1993 | Watson | 604/8 |
| 5,207,684 | 5/1993 | Nobles | 606/108 |
| 5,257,630 | 11/1993 | Broitman et al. | 128/675 |
| 5,304,114 | 4/1994 | Cosman et al. | 604/8 |
| 5,325,865 | 7/1994 | Beckman et al. | 128/748 |
| 5,336,166 | 8/1994 | Sierra | 604/9 |
| 5,368,556 | 11/1994 | Lecuyer | 604/8 |
| 5,387,188 | 2/1995 | Watson | 604/8 |
| 5,405,316 | 4/1995 | Magram | 604/8 |
| 5,437,626 | 8/1995 | Cohen et al. | 604/8 |
| 5,458,606 | 10/1995 | Cohen et al. | 604/108 |
| 5,464,144 | 11/1995 | Guy et al. | 227/176 |
| 5,497,934 | 3/1996 | Brady et al. | 227/176.1 |
| 5,503,320 | 4/1996 | Webster et al. | 227/176.1 |
| 5,637,083 | 6/1997 | Bertrand et al. | 604/9 |
| 5,643,194 | 7/1997 | Negre | 604/8 |
| 5,643,195 | 7/1997 | Drevet et al. | 604/9 |

FOREIGN PATENT DOCUMENTS

4427583  2/1996  Germany ................ A61M 39/00

*Primary Examiner*—John G. Weiss
*Assistant Examiner*—Ki Yong O
*Attorney, Agent, or Firm*—Nutter, McClennen & Fish, LLP

[57] ABSTRACT

A cerebrospinal fluid (CSF) shunt valve includes a valve housing and a substantially flat stabilizing member that has a width substantially greater than that of the valve housing. The shunt valve is adapted for surgical implantation under the scalp of a patient to drain excess CSF from the brain. The stabilizing member rests on the skull of a patient and the stabilizing member is effective to prevent rotation of the shunt valve about a longitudinal axis thereof. The shunt valve includes a pressure adjustment mechanism disposed within the housing, for adjusting a threshold pressure at which fluid may flow through the shunt valve.

10 Claims, 6 Drawing Sheets

PEDIATRIC PROGRAMMABLE HYDROCEPHALUS VALVE

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

Catheters of various types are used to drain fluid from different areas of the body of a patient. One application of such catheters is for the treatment of hydrocephalus, a condition where cerebrospinal fluid (CSF) collects in the ventricles of the brain of a patient. CSF is produced by the ventricular system and is normally absorbed by the venous system. However, If the CSF is not absorbed, the volume of CSF increases thereby elevating the intracranial pressure. This excess CSF can result in abnormally high epidural and intradural pressures. Left untreated, hydrocephalus can result in serious medical conditions, including subdural hematoma, compression of the brain tissue and impaired blood flow.

Various drainage catheters or shunt systems have been developed to remove the excess CSF and to discharge the fluid to another part of the body, such as the peritoneal region. By draining the excess fluid, the elevated intracranial pressure is relieved.

Generally, fluid shunt systems include a valve mechanism for controlling or regulating the flow rate of fluid through the system. An illustrative shunt system includes a valve mechanism in fluid communication with a brain ventricular catheter. The ventricular catheter is inserted into a ventricle of the brain and a peritoneal catheter is inserted into the peritoneal region for discharge of the fluid. Exemplary shunt systems include U.S. Pat. Nos. 4,332,255, 4,387,715, 4,551,128, and 3,886,948, all of which are incorporated by reference herein.

Figure 1:
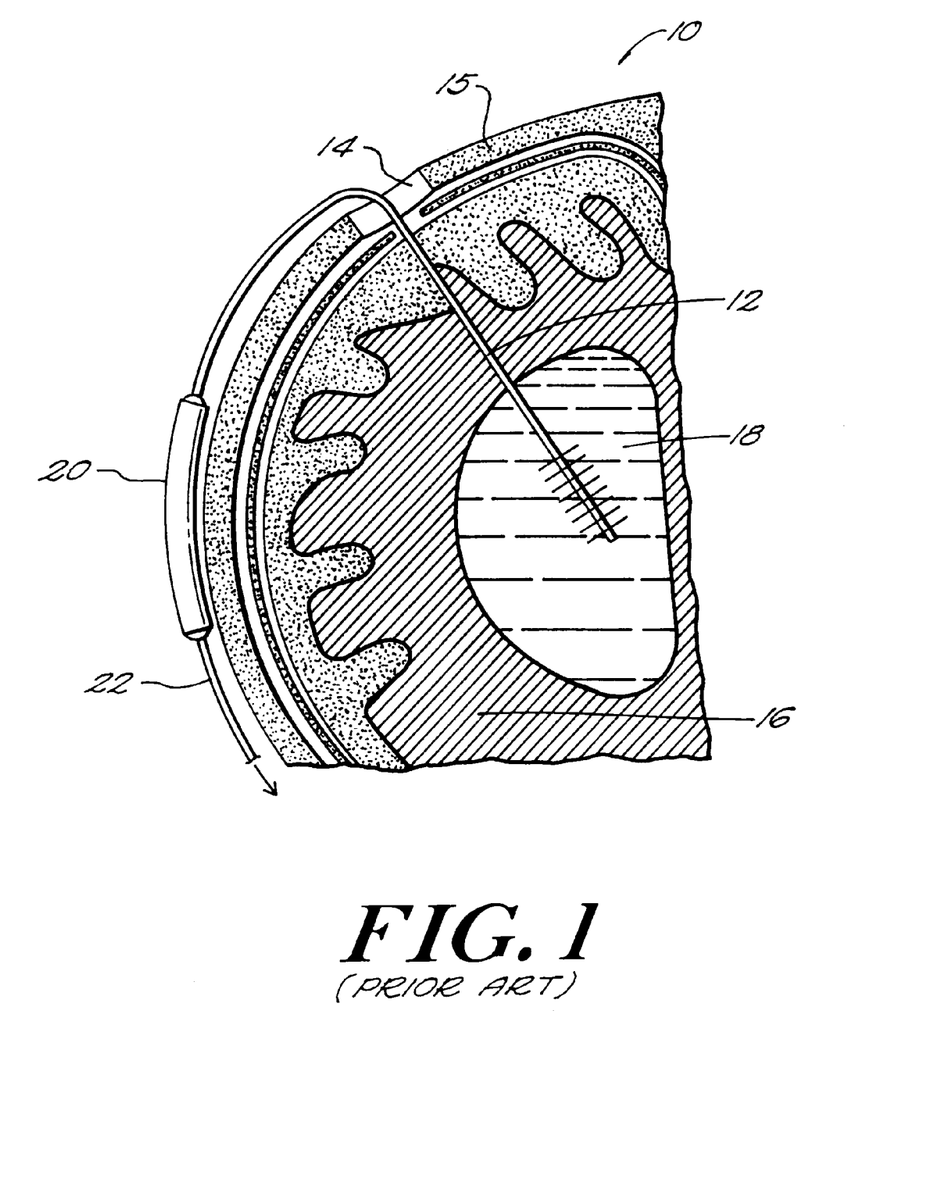
FIG. 1 is a pictorial representation of a prior art ventricular catheter.

FIG. 1 shows a prior art shunt system 10 having a ventricular catheter 12 inserted through a hole 14 in the skull 15 of a patient. The catheter 12 is advanced through brain tissue 16, and into a ventricle 18 of the brain where excess CSF is present. The catheter 12 is coupled to an inlet end of a shunt valve 20 and a drainage catheter 22 is coupled to an outlet end of the shunt valve. The shunt valve 20 is typically implanted under the scalp (not shown) of the patient The shunt system is operative to drain excess CSF from the ventricle to another part of the body, such as the right atrium, peritoneal cavity, or other locations in the body.

Shunt systems typically permit fluid flow only when the fluid pressure reaches a threshold pressure for the shunt valve. The fluid flow rate is proportional to the pressure at the valve mechanism. Thus, for a pressure slightly greater than the threshold pressure, the flow rate is relatively low. As the pressure increases the flow rate through the shunt system concomitantly increases. At pressures significantly greater than the threshold pressure, a maximum flow rate for the system is reached. Fluid flow normally continues until the intracranial pressure has been reduced to a level less than the threshold pressure, subject to any hysteresis of the device.

The threshold pressure that allows fluid flow through a shunt system must often be adjusted. For example, a surgeon may initially select a relatively low threshold pressure to trigger fluid flow. Over time, the initial threshold pressure may not be ideal. For example, it could lead to excess fluid flow, creating an undesirable overdrainage condition in which too much fluid is drained from the ventricle. Such a situation may give rise to a need to increase the threshold pressure to afford a fluid flow rate that is balanced to avoid both excessive intracranial pressure and overdrainage conditions.

The hydrocephalus shunt system is surgically implanted, and adjustment of the threshold pressure often requires the system to be surgically removed, adjusted, and then surgically implanted again. If the valve is not adjusted correctly, or if the intracranial pressure of the patient changes over time, then the valve must be re-adjusted, i.e., surgically removed and re-implanted.

One prior art shunt valve that allows threshold pressure adjustment without removal of the device is disclosed in U.S. Pat. Nos. 4,615,691 and 4,772,257, both of which are incorporated by reference herein. These patents disclose a cerebrospinal fluid shunt valve that is externally adjustable by means of a programming device. The shunt valve includes a stepping motor having rotor and stator elements. The stator elements are composed of a magnetically soft and permeable material shaped and positioned with respect to the rotor. The external programming device applies a magnetic field causing the rotor to rotate about a central axis so as to adjust the threshold pressure.

The programming device includes a surface having a groove therein for accommodating a protrusion on the scalp of a patient caused by the implanted shunt valve. The device includes a plurality of generally coplanar electromagnets disposed about a central axis. To adjust the shunt valve, the programming device is first placed against the head of the patient so that the scalp protrusion is within the groove of the device. An operator verifies the longitudinal position of the shunt valve within the groove to enable proper pressure adjustment. The central axis of the electromagnets and rotor should be substantially coaxial to ensure accurate programming of the valve. Once the proper position is achieved, the electromagnets in the programming device are energized to apply a magnetic field to actuate the stepper motor and select a predetermined threshold pressure for the valve mechanism.

Proper alignment of the axes can be difficult to achieve because an operator cannot see the rotor or the stator elements. This difficulty is further compounded by the rather small size of these elements relative to the electromagnets. Although the device can tolerate some degree of axial misalignment, the reliability of the external programming device degrades as the degree of misalignment increases.

Misalignment can occur due to rotation of the shunt valve under the patient's scalp. The external programmer must be placed adjacent to the top surface of the shunt system. Any rotation or rolling of the system will misalign the system, making external adjustment difficult or impossible.

The shunt valve is typically disposed in a generally rectangular housing with rounded corners. The valve has an aspect ratio with respect to height and width that is approximately unity, making it somewhat prone to rolling. The valve can also be housed within a generally circular silicone housing that further contributes to a rounding of the valve, creating further rotational instability. Thus, the shunt valve and stepper motor rotor can easily displace from a programmable position where the rotor axis is normal to a portion of the skull where the valve is located. Under certain conditions, such as a well placed impact, the valve can rotate forty-five degrees or more, thus rendering the programming device useless and requiring surgical removal of the valve in order to effect pressure adjustment.

SUMMARY OF THE INVENTION

The present invention provides a surgically implantable shunt system that is useful to drain fluid from one part of a patient's body to another. In one embodiment, the device is a shunt system implantable within the cranium for draining excess cerebrospinal fluid (CSF). Although the device is primarily described and illustrated as a CSF shunt valve, it is understood that it can be used for other types of implantable valve systems as well.

The shunt valve includes a housing having top and bottom portions and sidewalls that define a housing width. The housing also includes an inlet aperture and an outlet aperture for allowing fluid flow through the device. A valve element or a similar mechanism able to regulate the rate of fluid flow is disposed within the housing. Preferably the valve element is such that it permits external adjustment of a threshold pressure above which fluid can flow through the valve. In one embodiment, the valve element includes a stepper motor that can be actuated by an external programming device that applies a magnetic field. The programming device allows a user to adjust the threshold pressure of the valve above which fluid flows through the device to allow drainage of CSF through the shunt system. However, the relative position of the programming device with respect to the valve element must be such that the programming device can apply the magnetic field at an orientation that actuates the stepper motor.

The shunt valve system of the invention further includes a stabilizing member that is either integral with or attached to the bottom portion of the housing. The stabilizing member has a substantially flat bottom surface adapted for placement on, or proximate, the skull of a patient. The flat bottom surface of the stabilizing member extends beyond the width of the housing to increase rotational stability and to prevent rotation of the device with respect to the skull. The stabilizing member helps to prevent rotation of the shunt valve with respect to the skull, thus ensuring that the external programming device can effectively adjust the threshold pressure of the shunt valve without surgical removal.

BRIEF DESCRIPTION OF THE DRAWINGS

The invention will be more fully understood from the following detailed description taken in conjunction with the accompanying drawings, in which.

DETAILED DESCRIPTION OF THE INVENTION

FIGS. 2A–D show a prior art externally programmable shunt valve system 50 and an external programming device 52 for adjusting a threshold pressure at which fluid begins to flow through the device. The shunt valve 50 is typically surgically implanted under the scalp of a patient. The programmer 50 includes a control device 54 for selecting a threshold pressure and a programming element 56 that is placed over the scalp protrusion that is created by the implanted shunt valve. The shunt valve 50 includes a stepper motor 58 that is actuated by a magnetic field applied by the programming element 56 to adjust the threshold pressure of the shunt valve.

Figure 2A:
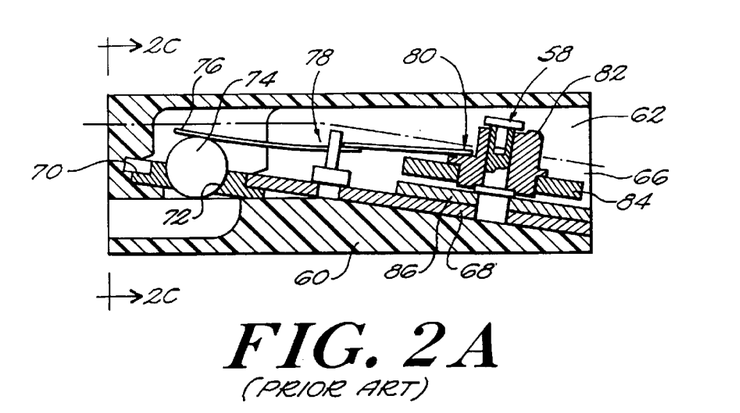
FIG. 2A is a side, sectional view of a prior art externally programmable shunt valve.

The shunt valve 50 includes a valve body 60 defining a chamber 62 with an inlet opening 64 and an outlet opening 66. When a fluid pressure at the inlet opening exceeds the predetermined threshold, fluid begins to flow through the shunt valve via the inlet and outlet openings 64,66. A support plate 68 is disposed within the valve body 60 and includes an aperture 70 at one end that is provided with a valve seat 72. A ball 74 is adapted for sealing engagement with the valve seat 72. A first end 76 of a spring 78 biases the ball to the valve seat 72 to prevent fluid flow. The biasing force of the spring 78 is adjustable by varying the vertical position of the spring at a second end 80, which can be adjusted by means of a cam 82. The cam 82 includes a plurality of steps of varying vertical position with respect to the plate 68. Each step provides a discrete pressure on the ball 74 via the spring 78. The biasing force provided by the spring 78 determines the threshold pressure that must be overcome in order to separate the ball from the valve seat and allow fluid flow into the chamber 62.

The cam 82 is disposed in a centrally located hole in a rotor 84 which includes a plurality of permanent magnetic poles of alternate polarity. At any one angular position, a pole exposed on the top side has an opposite pole on the other side. Below the rotor 84, four stator elements are fixed in a stator member 86. The stator elements are formed from a magnetically soft and permeable material. The stator elements are shaped to conform to the rotor 84 elements.

Figure 2B:
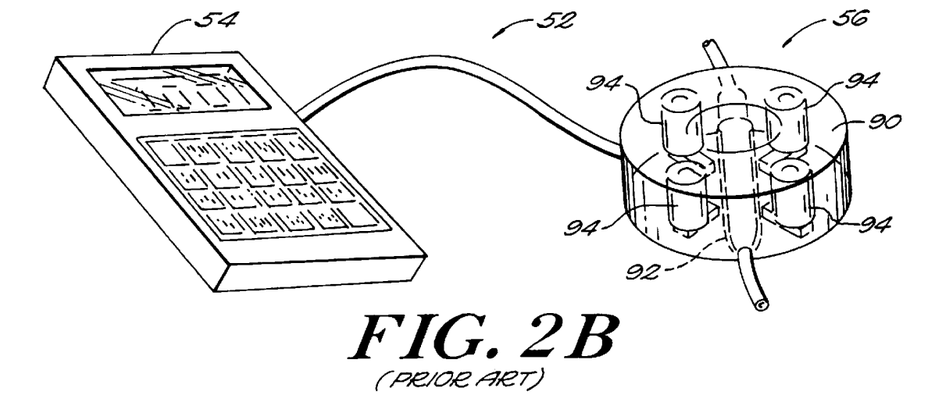
FIG. 2B is perspective view of a prior art programmer for programming the prior art shunt valve of FIG. 2A.

After surgical implantation of the shunt valve 50 under the scalp of a patient, the threshold pressure can be adjusted by using the programmer 52. The programming element 56 of the programmer includes a housing 90 having a groove 92 adapted to conform to a protrusion on the scalp caused by the implanted shunt valve. An operator maneuvers the programming element 56 so that the scalp protrusion is within the groove 92. Thereafter, a series of electromagnets 94 disposed about a central axis are sequentially energized to apply a pulsed magnetic field to the stepper motor and cause the rotor to rotate. This causes the cam 82 to rotate and therefore adjust the pressure applied to the ball 74 by the first end 76 of the spring. In this manner, the threshold pressure of the shunt valve is adjusted.

Ideally, the central axis of the electromagnets is coaxial with the axis defined by rotation of the rotor 84. Exact alignment of theses axes is not necessary and the programmer is tolerant of some misalignment. However, as the degree of misalignment increases, the accuracy and reliability of the programmer decreases. Further, if the implanted shunt valve rotates a significant amount about its longitudinal axis x, such as more than about forty-five degrees, the shunt valve can no longer be programmed.

Figure 2C:
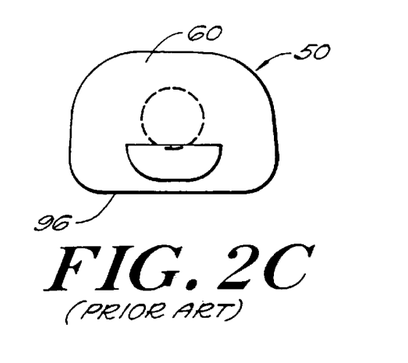
FIG. 2C is an elevation view taken at lines 2C—2C of the prior art shunt valve of FIG. 2A.
Figure 2D:
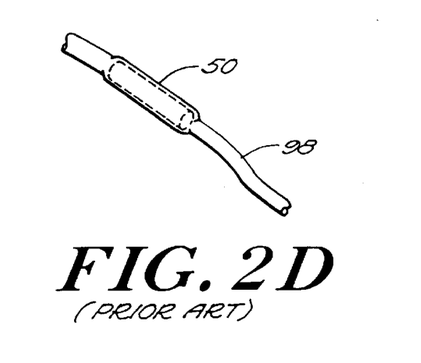
FIG. 2D is a perspective view of the prior art shunt valve of FIG. 2A shown inserted within the generally circular silicone housing.

As shown in FIG. 2C, the valve 50 has a valve body 60 with a generally rectangular cross section, rounded corners and a non-planar bottom surface 96 that is adapted for placement against the scalp. This shape facilitates insertion of the shunt valve 50 into a generally circular silicone housing 98. However, the geometry of the valve body 60 is somewhat unstable and the shunt valve is prone to rotation about its longitudinal axis x. Rotation of the shunt valve can occur spontaneously, or it can be caused by an impact or a force applied to the shunt valve. This tendency toward rotation can be further compounded by the generally circular silicone housing 98 surrounding the shunt valve which contributes to the rounding of the corners of the valve body.

Figure 3:
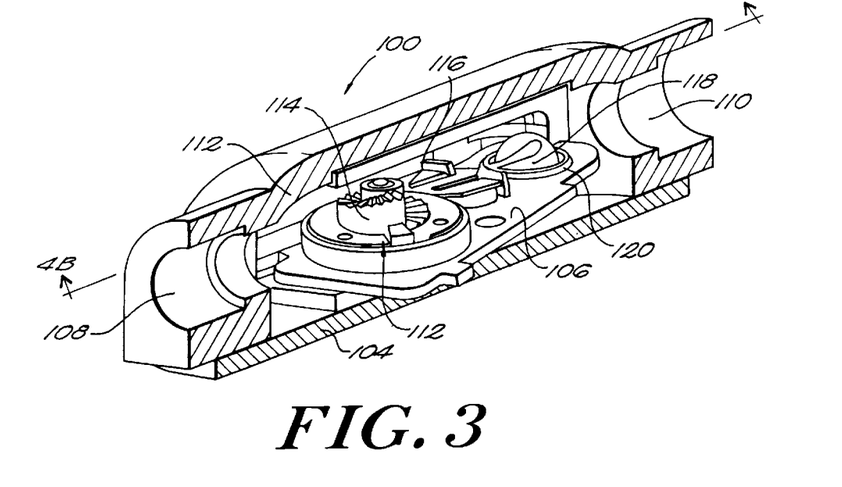
FIG. 3 is a cutaway perspective view of a shunt valve in accordance with the present invention.

FIG. 3 illustrates a shunt valve 100 in accordance with the present invention. The shunt valve 100 includes a housing or valve body 102 and a separate, substantially flat stabilizing member 104 bonded to the valve body. The valve body 102 defines an outlet aperture 108 and an inlet aperture 110. An element for regulating fluid flow through the shunt valve, such as valve 106, is disposed within the valve body 102 for controlling the flow rate of fluid through the device. In an exemplary embodiment, the valve 106 is an adjustable valve mechanism including a stepper motor 112 having a fixed stator and a rotor for turning cam 114 to adjust the vertical height of spring 116 and thereby adjust the threshold pressure that biases ball 118 into valve seat 120.

Figure 4A:
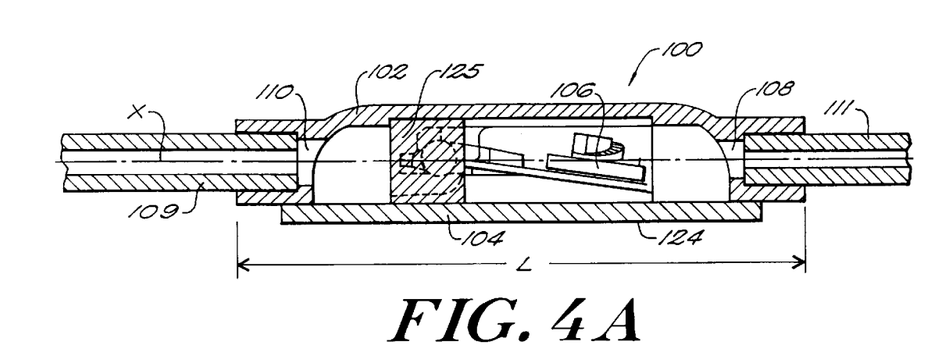
FIG. 4A is a side, sectional view of the shunt valve of FIG. 3.
Figure 4B:
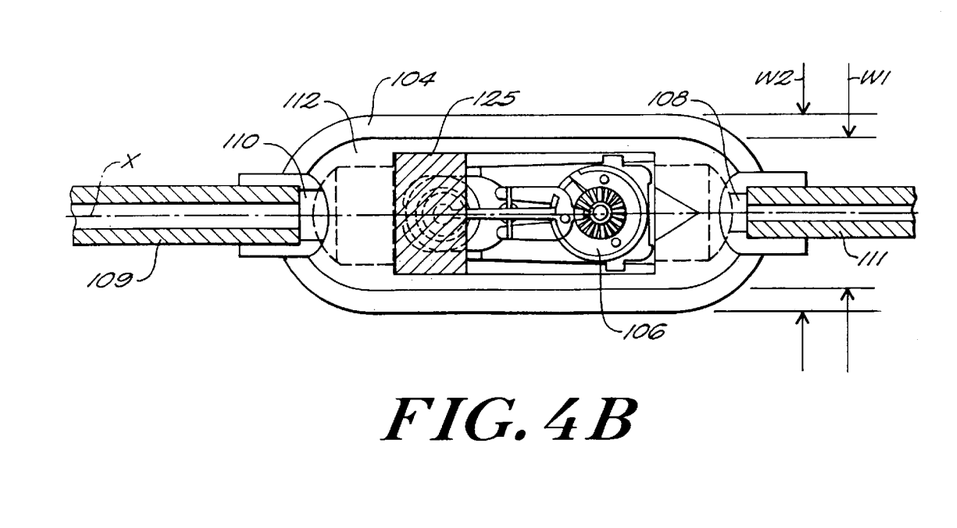
FIG. 4B is a top, sectional view of the shunt valve of FIG. 3 at lines 4B—4B.
Figure 4C:
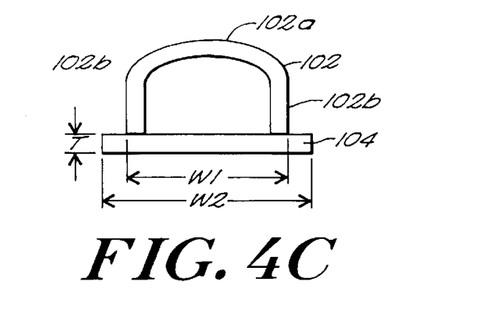
FIG. 4C is an end view of the shunt valve of FIG. 3.

FIGS. 4A–C show further details of the shunt valve 100. The housing or valve body 102 includes a top surface 102$a$ and sidewalls 102$b$ that define a first width W1. The shunt valve 100 has a length L with respect to a longitudinal axis X of the shunt valve. The stabilizing member 104 has a thickness T and includes a bottom surface 124 that has a second width W2 that is substantially greater than the width W1 of the housing 102. Thus, the stabilizing member 104 laterally extends beyond the valve body to decrease the height/width aspect ratio of the shunt valve. This design possesses inherent rotational stability, making the shunt valve 100 more reliable and more easily and accurately externally programmable.

The valve body 102 may have a width W1 that ranges from about 0.20 to 1.00 inch. More preferably the W1 dimension is about 0.25 inch. The width (W2) of the stabilizing member 104 preferably is about 0.06 to 0.40 inch greater than the W1 dimension. Preferably, the stabilizing member 104 has a width (W2) that is about 0.10 to 0.20 inch greater than W1. In embodiments in which the housing 102 is centered on the stabilizing member, the stabilizing member preferably extends beyond the sidewalls 102$b$ of the housing 102 by about 0.055 to 0.060 inch. One of ordinary skill in the art will appreciate that the dimensions of the housing 102 can vary and that such variations in the housing dimensions will influence the width of the stabilizing member 104. Generally, the height/width aspect ratio of the valve 100 should be maintained in the range of about 0.20 to 0.35 to achieve the desired rotational stability.

In the embodiment of FIGS. 3–4C, the stabilizing member 104 is a separate element that is bonded to the bottom 102$c$ of housing 102. The stabilizing member 104 can be bonded with a suitable adhesive that is biocompatible and compatible with the valve body and stabilizing member. The adhesive must be permanent and strong, yet allow the stabilizing member to flex to the match the skull contour. Exemplary adhesives include silicone adhesives such as Dow-Corning medical adhesive "A" or similar materials. Bonding may also be effected by other techniques, such as compression and thermal curing of uncured silicone.

Figure 4D:
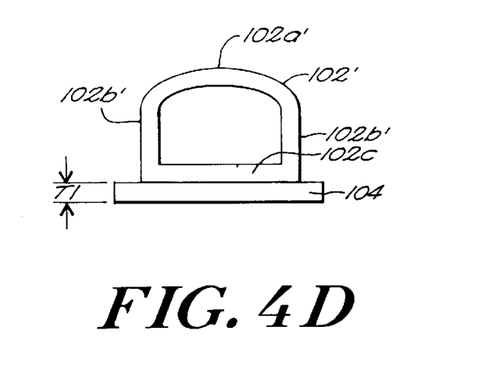
FIG. 4D is an end view of an alternative embodiment of the shunt valve of FIG. 3.

FIG. 4D is an alternative embodiment to the shunt valve of FIGS. 4A–C that includes a housing 102' having a bottom surface 102$c$ spanning the length of the housing and extending from one sidewall 102$b$ of the housing to the other sidewall. The bottom surface 102$c$ of the housing can be adhesively bonded to the stabilizing member 104 as described above. The bottom surface 102$c$ has a thickness T1 that can range from about 0.020 to 0.040 inch and preferably is about 0.030 inch.

The length of the shunt valve can vary, depending on the requirements of a particular device. Generally, however, the length ranges from about 0.5 inch to 3.0 inches. In an exemplary embodiment, the length L of the valve body is about 0.90 inch.

The thickness T of the stabilizing member can vary depending upon the requirements of a given application. The thickness T affects the rigidity of the shunt valve 100. Thus, the thickness should not be so great as to prevent the stabilizing member from conforming to the curvature of a patient's skull. Generally, the thickness T is in the range of about 0.015 to 0.040 inch, and more preferably is about 0.020 inch.

The stabilizing member 104 and the valve body 102 can be made from a variety of biocompatible materials suitable for long term and/or permanent implantation within the body. Although not necessary, these components can be made of the same material. Suitable materials preferably are semi-rigid, allowing the stabilizing member to conform to the curvature of the skull. However, the material should not be so flexible as to allow an amount of bending of the stabilizing member 104 in an axis transverse to longitudinal axis X. Exemplary materials include polymers, such as polyurethane, silicones, polyethylenes, polypropylenes, and metals such as titanium, titanium alloys and stainless steel. A preferred material is medical grade silicone made by Dow-Corning or Nusil Silicone Technology.

Although the housing 102 is shown having a rounded top surface and opposed side walls, one of ordinary skill in the art will appreciate that other profiles are possible as well. For example, the housing can define a semicircular, triangular, or other such symmetrical or non-symmetrical cross sections.

As noted above, the low height/width aspect ratio of the shunt valve 100 resists rotation of the device about the longitudinal axis X. Ideally, the width of the stabilizing member 104 impedes rotation of the shunt valve and the shunt valve is able to remain on the skull of the patient in the preferred orientation. By maintaining the shunt valve in the desired, implanted orientation the valve mechanism remains in a programmable position. Thus, there is less likelihood that the valve may need to be surgically removed to adjust the threshold pressure.

A surgeon or another medical professional can ascertain the relative position of the shunt valve 100 through tactile examination of the scalp protrusion caused by the shunt valve. Such an examination is helpful to verify that the stabilizing member 104 remains against the skull of patient and that the valve has not rotated to any significant extent. The mechanism can also be oriented by x-ray to determine if the valve has rotated. A typically correct position of the valve is provided for comparison to the latest x-ray.

FIGS. 4A–B show the shunt valve having an adhesive seal band 125. The seal prevents flow around the valve mechanism in either direction within the silicone housing.

As illustrated in FIGS. 4A–4B, the shunt valve 100 can be coupled to tubing at the inlet aperture 110 and outlet aperture 108 to accommodate fluid flow from one body location to another. For example, an inlet tube 109 is coupled to the inlet aperture 110 to divert CSF from the ventricular catheter to the shunt valve. An outlet tube 111 is coupled to the outlet aperture 108 to provide a CSF discharge conduit from the shunt valve to another location in the body.

In another embodiment (not shown), the entire shunt valve is inserted into a generally circular silicone housing. In this embodiment, the shunt valve occludes the tube such that any fluid flow through the tubing must pass through the valve 100 via inlet aperture 110 and outlet aperture 108.

Figure 5:
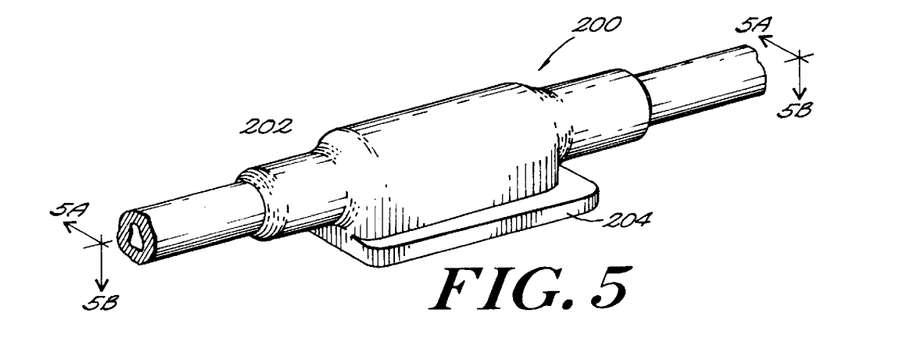
FIG. 5 is a perspective view of another embodiment of a shunt valve in accordance with the present invention.
Figure 5A:
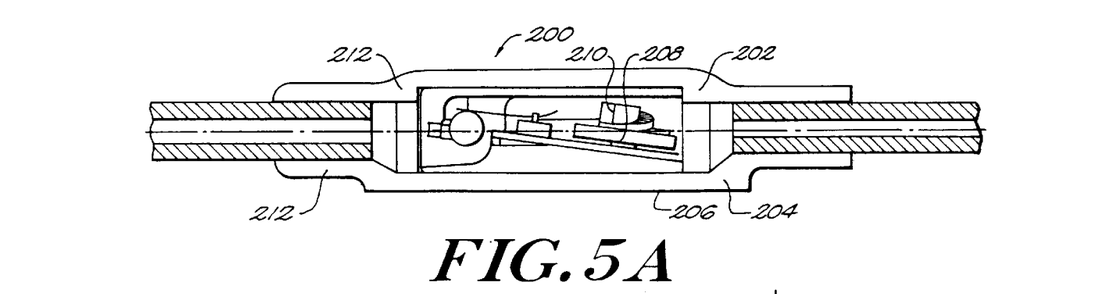
FIG. 5A is a side, sectional view of the shunt valve of FIG. 5 at lines 5A—5A.
Figure 5B:
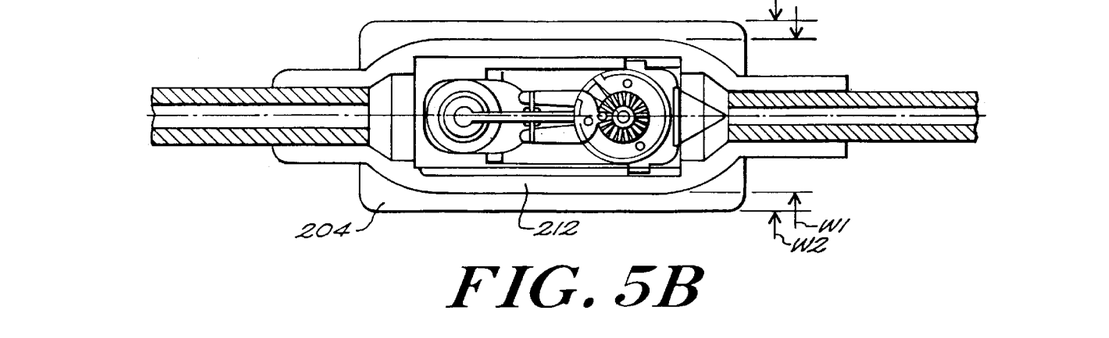
FIG. 5B is a top, sectional view of the shunt valve of FIG. 5 at lines 5B—5B.
Figure 5C:
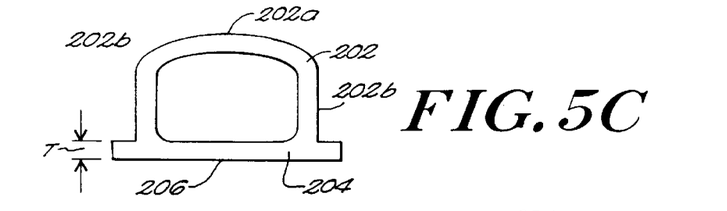
FIG. 5C is an end view of a housing of the shunt valve of FIG. 5.

FIGS. 5–5C show a further embodiment of a fluid shunt valve 200 in accordance with the present invention. The shunt valve 200 includes a valve housing 202 having a stabilizing portion 204 with a substantially flat bottom stabilizing surface 206. The stabilizing portion 204 is integrally formed with the valve housing 202. A valve mechanism 208 is disposed within the valve housing 202 and establishes a threshold pressure necessary to initiate fluid flow through the shunt valve. The valve mechanism 208 may be of a type, as discussed above, that includes a stepper motor 210 that is actuable by an externally applied magnetic field to adjust the threshold pressure.

The valve housing 202 includes the stabilizing portion 204 that is integrally joined to upper housing 212. Upper housing 212 includes a top wall 202a and opposed side walls 202b.

The upper portion 212 has a width W1 that is less than a width W2 of the stabilizing portion 204. Generally, the W2 dimension can range from about 0.06 to 0.40 inch greater than W1, and preferably from about 0.06 to 0.20 inch greater than W1. In an exemplary embodiment, W2 is about 0.30 inch and W1 is about 0.24 inch, allowing the stabilizing portion 204 to extend a total of about 0.06 inch beyond the side walls 202b of the valve housing 202. In one embodiment, the upper portion 212 is centrally disposed on stabilizing portion 204, and portion 204 extends about 0.03 on each side of the valve body 202. The width of the upper portion 212 and/or stabilizing portion 204 can be substantially constant over the length of the shunt valve, or this dimension may be variable.

The length of the shunt valve 200 can range from about 0.50 inch to about 1.50 inches. The stabilizing portion 204 of the shunt valve has a thickness T that can vary from about 0.02 to 0.04. In an exemplary embodiment, the shunt valve length is about 0.70 inch and the thickness T of the stabilizing portion 204 is about 0.03 inch.

Figure 6:
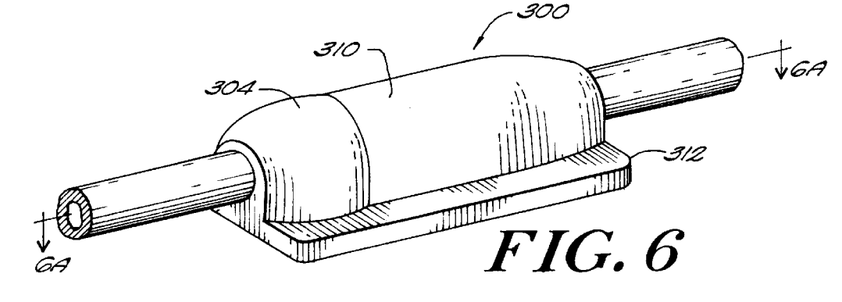
FIG. 6 is a perspective view of a further embodiment a shunt valve in accordance with the present invention.
Figure 6A:
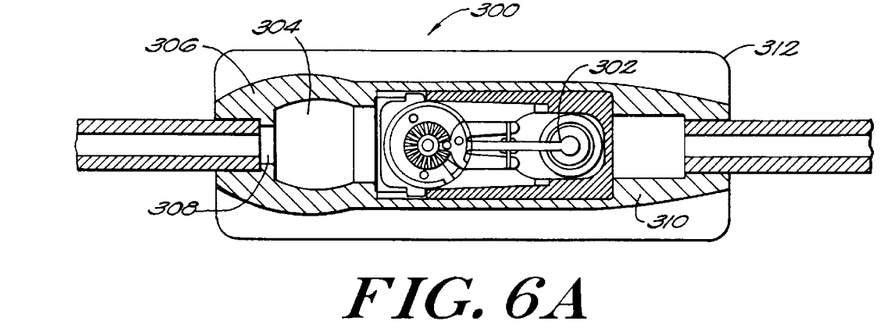
FIG. 6A is a top, sectional view of the shunt valve of FIG. 6 at lines 6A—6A.

FIGS. 6 and 6A illustrate another embodiment of a shunt valve assembly 300 having a valve mechanism 302 and a pumping chamber 304 for pumping fluid downstream of the shunt valve. The pumping chamber 304 is actuated by applying pressure to a flexible portion 306 of the assembly that is disposed above the pumping chamber 304. In an illustrative embodiment, the pumping chamber 304 is disposed adjacent an outlet opening 308 of the valve mechanism 302.

The shunt valve assembly 300 includes a housing 310 in which the valve mechanism 302 and/or pumping chamber 304 are disposed. Assembly 300 further includes a substantially flat stabilizing member 312. As described above, the stabilizing member 312 can be a separate member that is bonded to the housing 310 or it can be integrally formed with the housing. The stabilizing member 312 has the properties described above with respect to stabilizing member 104 and 204. That is, stabilizing member 312 is substantially wider than the valve housing 310 so that it can prevent rotation of the assembly after implantation of the assembly under the scalp of a patient. In an exemplary embodiment, the stabilizing member 312 has a width that is greater than a width of the valve housing 310 by an amount that ranges from about 0.05 to 0.20 inch.

Figure 7:
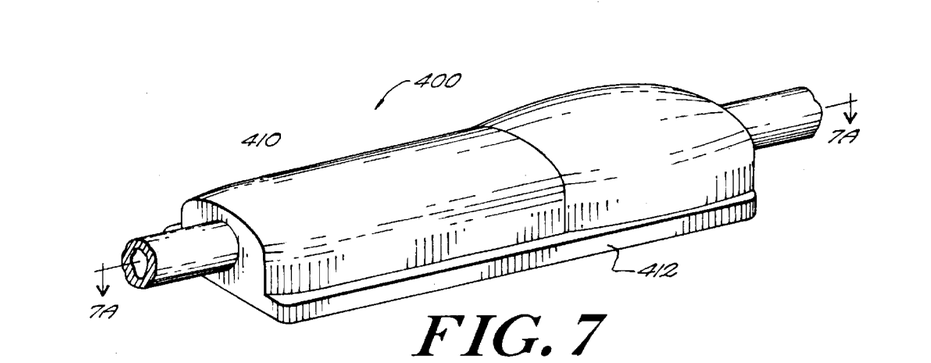
FIG. 7 is a perspective view of a still further embodiment of a shunt valve in accordance with the present invention.
Figure 7A:
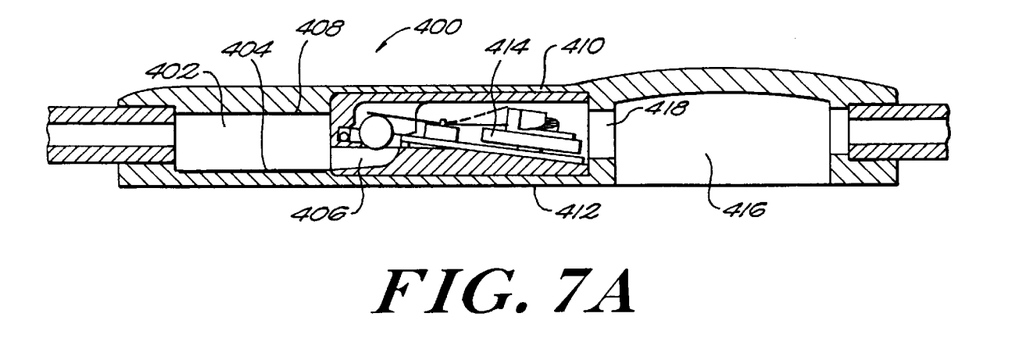
FIG. 7A is a side, sectional view of the shunt valve of FIG. 7 at lines 7A—7A.

FIGS. 7 and 7A show a shunt valve assembly 400 having an injection area 402 with an impenetrable needle stop 404 for maintaining a needle within the injection area. In an exemplary embodiment, the injection area 404 is disposed in fluid communication with an inlet opening 406 of the assembly. A syringe can be inserted through the scalp and then through a wall 408 of the injection area 402 to inject drugs or other liquids into the injection area. The injection area 402 also provides a source from which a fluid sample can be withdrawn. The needle stop 404 is effective to prevent the syringe from passing out of the injection area and through the bottom of the assembly.

In an exemplary embodiment, the needle stop 404 is formed from titanium, stainless steel, or titanium alloys, or other suitable material that is biocompatible and penetration resistant.

The shunt valve assembly 400 includes a housing 410 and a substantially flat stabilizing member 412 integral with the housing or separately bonded thereto as described above. A valve mechanism 414, of the type described above, is disposed within the housing 410. Preferably, the valve 414 provides a threshold pressure above which fluid is permitted to flow through the device. The valve mechanism 414 can include a stepper motor actuated by an externally applied magnetic field. Further, the shunt valve assembly 400 can optionally include a pumping chamber 416 disposed at an outlet opening 418 of the assembly, as described above with respect to FIGS. 6 and 6A.

The properties and dimensions of the stabilizing member 412 are as described above with respect to FIGS. 3–6A. It is understood that the width of the stabilizing member must sufficiently exceed that of the housing 410 to prevent rotation of the assembly 400 after implantation.

It will be understood that the foregoing is only illustrative of the principles of the invention, and that various substitutions and modifications can be made by those skilled in the art without departing from the scope and spirit of the invention. All cited references are expressly incorporated herein by reference in their entirety.

What is claimed is:

1. A bioimplantable, pediatric, Hakim-type shunt valve for regulating the flow of fluid from one location within a body of a child to another location within the body, comprising:

an elongate housing made of a biologically implantable material and having top and bottom surfaces and sidewalls that define a housing width, the top surface being generally hemispherical, and the housing having an inlet aperture and an outlet aperture;

a valve mechanism for regulating a rate of fluid flow through the shunt valve, the valve mechanism being disposed within the housing, wherein the valve mechanism includes a stepper motor that is actuable by an external programming device aligned with the stepper motor in a predetermined position; and a stabilizing member secured to the housing, the stabilizing member having a first surface adjacent the bottom surface of the housing and a substantially planar bottom surface adapted for placement against a skull of the child, the bottom surface having a width that is greater than the width of the housing such that the stabilizing member is effective to maintain the stabilizing member in contact with the skull and to prevent rotation of the housing about a longitudinal axis thereof, wherein the housing has a length of less than about 0.9 inch and a width that is less than about 0.5 inch, and the stabilizing member has a width that is at least thirty percent larger than a width of the housing.

2. The shunt valve according to claim 1, wherein the stabilizing member is centered about the longitudinal axis of the housing so that the flat bottom surface extends a substantially equal amount on either side of the housing.

3. The shunt valve according to claim 1, wherein the valve mechanism may be adjusted to select a predetermined threshold pressure above which fluid is permitted to flow from the inlet aperture to the outlet aperture.

4. The shunt valve according to claim 3, wherein the the predetermined threshold pressure is selectable by an electromagnetic field applied by the external programming device.

5. The shunt valve according to claim 1, wherein the stabilizing member is a separate member that is bonded to the housing.

6. The shunt valve according to claim 1, whenever the stabilizing member is integrally formed with the housing.

7. The shunt valve according to claim 1, wherein the stabilizing member is semi-rigid and adapted to substantially conform to a surface of the skull.

8. A pediatric, Hakim-type shunt valve subcutaneously implantable on the skull of a child, comprising:

a housing having an upper portion defining a first width and a lower, substantially planar stabilizing surface defining a second width larger than the first width, the stabilizing surface being adapted for placement on the skull of the child and being effective to prevent rotation of the shunt valve about a longitudinal axis of the housing; and a valve mechanism disposed within the housing for allowing fluid to flow through the shunt valve, from an inlet opening of the housing to an outlet opening of the housing, when a fluid pressure at the inlet opening is greater than a predetermined threshold pressure, the valve mechanism including a stepper motor for selecting the threshold pressure which is adjustable by an external programming device aligned with the stepper motor in a predetermined position, wherein the housing has a length less than about 0.9 inch, the first width is less than about 0.25 inch, and the second width is greater than the first width by at least 0.1 inch.

9. The shunt valve according to claim 1, wherein the upper portion of the housing is substantially centered with respect to the stabilizing surface of the housing.

10. The shunt valve according to claim 8, wherein the predetermined threshold pressure of the valve mechanism is externally adjustable by an externally applied magnetic field.

* * * * *